United States Patent
Hayashi et al.

(10) Patent No.: US 8,023,111 B2
(45) Date of Patent: Sep. 20, 2011

(54) SURFACE INSPECTION APPARATUS

(75) Inventors: Yoshinori Hayashi, Yokohama (JP); Masao Kawamura, Yokohama (JP); Hideki Mori, Yokohama (JP)

(73) Assignee: Shibaura Mechatronics Corporation, Yokohama-shi (JP)

( * ) Notice: Subject to any disclaimer, the term of this patent is extended or adjusted under 35 U.S.C. 154(b) by 0 days.

(21) Appl. No.: 12/595,699

(22) PCT Filed: Apr. 25, 2008

(86) PCT No.: PCT/JP2008/058124
§ 371 (c)(1),
(2), (4) Date: Oct. 13, 2009

(87) PCT Pub. No.: WO2008/136432
PCT Pub. Date: Nov. 13, 2008

(65) Prior Publication Data
US 2010/0066998 A1   Mar. 18, 2010

(30) Foreign Application Priority Data
Apr. 27, 2007   (JP) .................................. 2007-120174

(51) Int. Cl.
*G01N 21/88* (2006.01)
(52) U.S. Cl. ................................... 356/237.5
(58) Field of Classification Search .................. None
See application file for complete search history.

(56) References Cited

U.S. PATENT DOCUMENTS
7,280,197 B1 *  10/2007  Rosengaus .................. 356/237.1

FOREIGN PATENT DOCUMENTS

| | | |
|---|---|---|
| JP | 9-269298 | 10/1997 |
| JP | 2002-310924 A1 | 10/2002 |
| JP | 2003-65960 A1 | 3/2003 |
| JP | 2004-191214 A1 | 7/2004 |
| JP | 2006-17685 A1 | 1/2006 |
| WO | WO 2006/059647 A1 | 6/2006 |

OTHER PUBLICATIONS

International Search Report for International Application No. PCT/JP2008/058124 dated Jul. 17, 2008.

* cited by examiner

*Primary Examiner* — Tu T Nguyen
(74) *Attorney, Agent, or Firm* — Kratz, Quintos & Hanson, LLP

(57) ABSTRACT

A semiconductor wafer inspection apparatus for inspecting an outer circumference edge part of a semiconductor wafer. The apparatus has a camera lens arranged facing an outer circumference edge part of a semiconductor wafer, an imaging surface arranged facing an outer circumference end face of a semiconductor wafer via the camera lens, a mirror forming an image of a first outer circumference bevel surface of the semiconductor wafer on the imaging surface via the camera lens, a mirror forming an image of a second outer circumference bevel surface of the semiconductor wafer on the imaging surface via the camera lens, a correction lens forming an image of an outer circumference end face of the semiconductor wafer on the imaging surface via the center part of the camera lens, and an illumination light guide lamp part illuminating the surfaces. With use of the apparatus the first outer circumference bevel surface and second outer circumference bevel surface become brighter compared with the outer circumference end face.

6 Claims, 11 Drawing Sheets

| IMAGE FORMED VIA TOP PART OF IMAGING LENS | IMAGE FORMED VIA CENTER OF IMAGING LENS | IMAGE FORMED VIA BOTTOM PART OF IMAGING LENS |

| ILLUM. UNIT END (ILLUMINATING 1ST OC BEVEL SURFACE) | ILLUM. UNIT CENTER (FIRING AT OC END FACE) | ILLUM. UNIT END (ILLUMINATING 2ND OC BEVEL SURFACE) |

SURFACE INSPECTION APPARATUS

CROSS-REFERENCES TO RELATED APPLICATIONS

This application claims priority from PCT application PCT/JP2008/058124 filed Apr. 25, 2008, which claims priority to Japan Application No. 2007/120174 filed Apr. 27, 2007.

TECHNICAL FIELD

The present invention relates to a surface inspection apparatus capturing an image of and inspecting an outer circumference edge part including a first outer circumference bevel surface slanted at an outer edge of a first main surface of a semiconductor wafer or other plate-shaped member, a second outer circumference bevel surface slanted at an outer edge of a second main surface of the plate-shaped member, and an outer circumference end face of the plate-shaped member.

BACKGROUND ART

In the past, the art of capturing an image of an outer circumference edge part of a semiconductor wafer and using that image to inspect the outer circumference edge part for damage, projections, and other conditions has been proposed. For example, the art described in Patent Literature 1 is a system for inspecting the state of the outer circumference edge part of a semiconductor wafer where the outer circumference edge part is comprised of an outer circumference end face, a first outer circumference bevel surface slanted at an outer edge of a first main surface, and a second outer circumference bevel surface slanted at an outer edge of a second main surface. This inspection apparatus arranges a camera lens facing the outer circumference edge part of the semiconductor wafer and forms an image of the outer circumference end face and forms images of the first outer circumference bevel surface and second outer circumference bevel surface on an imaging surface through the camera lens so as to be able to capture the outer circumference end face, first outer circumference bevel surface, and second outer circumference bevel surface all together.

Further, in the art described in Patent Literature 1, the length of the light path from the outer circumference end face of the semiconductor wafer to the imaging surface and the lengths of the light paths from the first outer circumference bevel surface and second outer circumference bevel surface to the imaging surface differ. It is difficult to form an image of the outer circumference end face and images of the first outer circumference bevel surface and second outer circumference bevel surface on a single imaging surface. In consideration of this, a correction lens is arranged between the outer circumference end face of the semiconductor wafer and the camera lens to make the lengths of the light paths match.

Patent Literature 1: International Publication No. 2006/059647 pamphlet

SUMMARY OF INVENTION

Technical Problem

However, due to aberration between the center part and peripheral parts of a camera lens etc., the image formed at the imaging surface has the characteristic that the image formed through the center part of the camera lens is higher in lightness and the images formed through the peripheral parts of the camera lens are lower in lightness. This difference in lightness is a problem in that it is not possible to suitably set detection conditions for the lightness in the inspection of the outer circumference edge part of a semiconductor wafer where detection of fine fluctuations in luminance or fluctuations in chroma is necessary. For example, if setting the detection conditions relating to lightness corresponding to the image formed through the center part of the camera lens, the images formed through the peripheral parts will be insufficient in lightness, while if setting the detection conditions relating to lightness corresponding to the images formed through the peripheral parts of the camera lens, the image formed through the center part will become excessive in lightness. The inspector will have a hard time obtain a grasp of the damage, projections, and other conditions at the outer circumference edge part.

The present invention was made in consideration of this situation and provides a surface inspection apparatus enabling suitable inspection of the outer circumference edge part of a semiconductor wafer or other plate-shaped member.

Solution to Problem

The surface inspection apparatus according to the present invention is a surface inspection apparatus capturing an image of and inspecting an outer circumference edge part including a first outer circumference bevel surface slanted at an outer edge of a first main surface of a plate-shaped member, a second outer circumference bevel surface slanted at an outer edge of a second main surface of the plate-shaped member, and an outer circumference end face of the plate-shaped member, the surface inspection apparatus having a camera lens arranged facing the outer circumference edge part of the plate-shaped member, an imaging surface arranged at an opposite side of the camera lens from the outer circumference edge part of the plate-shaped member, a first optical member forming an image of the first outer circumference bevel surface of the plate-shaped member on the imaging surface via a first peripheral part of the camera lens, a second optical member forming an image of the second outer circumference bevel surface of the plate-shaped member on the imaging surface via a second peripheral part of the camera lens, a third optical member forming an image of the outer circumference end face of the plate-shaped member on the imaging surface via a center part of the camera lens, and an illumination unit illuminating the outer circumference end face, the first outer circumference bevel surface, and the second outer circumference bevel surface so that compared with the outer circumference end face, the first outer circumference bevel surface and the second outer circumference bevel surface become brighter.

According to this constitution, it becomes possible to make the lightnesses of the images formed at the imaging surface as uniform as possible and suitably set the detection conditions relating to the lightness by considering the characteristic that the image formed at the imaging surface via the center part of the camera lens is high in lightness and the images formed at the imaging surface via the peripheral parts are low in lightness and illuminating the outer circumference end face, the first outer circumference bevel surface, and the second outer circumference bevel surface so that, compared with the outer circumference end face of the plate-shaped member, the first outer circumference bevel surface and second outer circumference bevel surface become brighter.

Further, the surface inspection apparatus according to the present invention may be configured so that the illumination unit illuminates the outer circumference end face, the first outer circumference bevel surface, and the second outer circumference bevel surface by an illuminance distribution giving a reverse relationship to the relationship of brightnesses of the image of the outer circumference end face, the image of the first outer circumference bevel surface, and the image of the second outer circumference bevel surface formed on the imaging surface via the camera lens when irradiating light of a constant illuminance distribution.

According to this constitution, it becomes possible to make the lightnesses of the images formed at the imaging surface as uniform as possible by irradiating light of illuminances having a reverse relationship to the relationship of lightnesses of the images formed at the imaging surface via the camera lens when the illumination unit irradiates light of a constant illuminance.

Further, the surface inspection apparatus according to the present invention may be configured so that the illumination unit has a light source and a plurality of illuminating surfaces arranged facing the outer circumference edge part of the plate-shaped member and irradiating light from the light source, and the illuminance of light irradiated from the illuminating surfaces arranged at the center part among the plurality of illuminating surfaces is smaller than the illuminances of light irradiated from the illuminating surfaces arranged at the end parts.

According to this constitution, it becomes possible to make the lightnesses of the images formed at the imaging surface as uniform as possible by having light irradiated from the illuminating surfaces arranged at the center part toward the outer circumference end face of the plate-shaped member and having light irradiated from the illuminating surfaces arranged at the end parts toward the first outer circumference bevel surface and second outer circumference bevel surface.

From a similar viewpoint, the surface inspection apparatus according to the present invention may be configured so that the illumination unit has a light source and a plurality of illuminating surfaces arranged facing the outer circumference edge part of the plate-shaped member and irradiating light from the light source, and a placement density at the center part of the plurality of illuminating surfaces is smaller than the placement densities at the end parts.

Further, the surface inspection apparatus according to the present invention may be configured so that the illumination unit has a cylindrical planoconvex lens arranged in front of the plurality of illuminating surfaces, and the illuminating surface side is flat.

According to this constitution, a cylindrical planoconvex lens is used to convert the light emitted from the illuminating surfaces to parallel light, so that parallel light can be irradiated toward the outer circumference end face, first outer circumference bevel surface, and second outer circumference bevel surface of the plate-shaped member.

Advantageous Effects of Invention

According to the present invention, it becomes possible to make the lightnesses of the images formed on the image surface as uniform as possible by illuminating the outer circumference end face, the first outer circumference bevel surface, and the second outer circumference bevel surface so that, compared with the outer circumference end face of the plate-shaped member, the first outer circumference bevel surface and second outer circumference bevel surface become brighter, so it becomes possible to suitably set the detection conditions relating to the lightness and suitably inspect the outer circumference edge parts of the plate-shaped member.

REFERENCE SIGNS LIST

Figure 1:
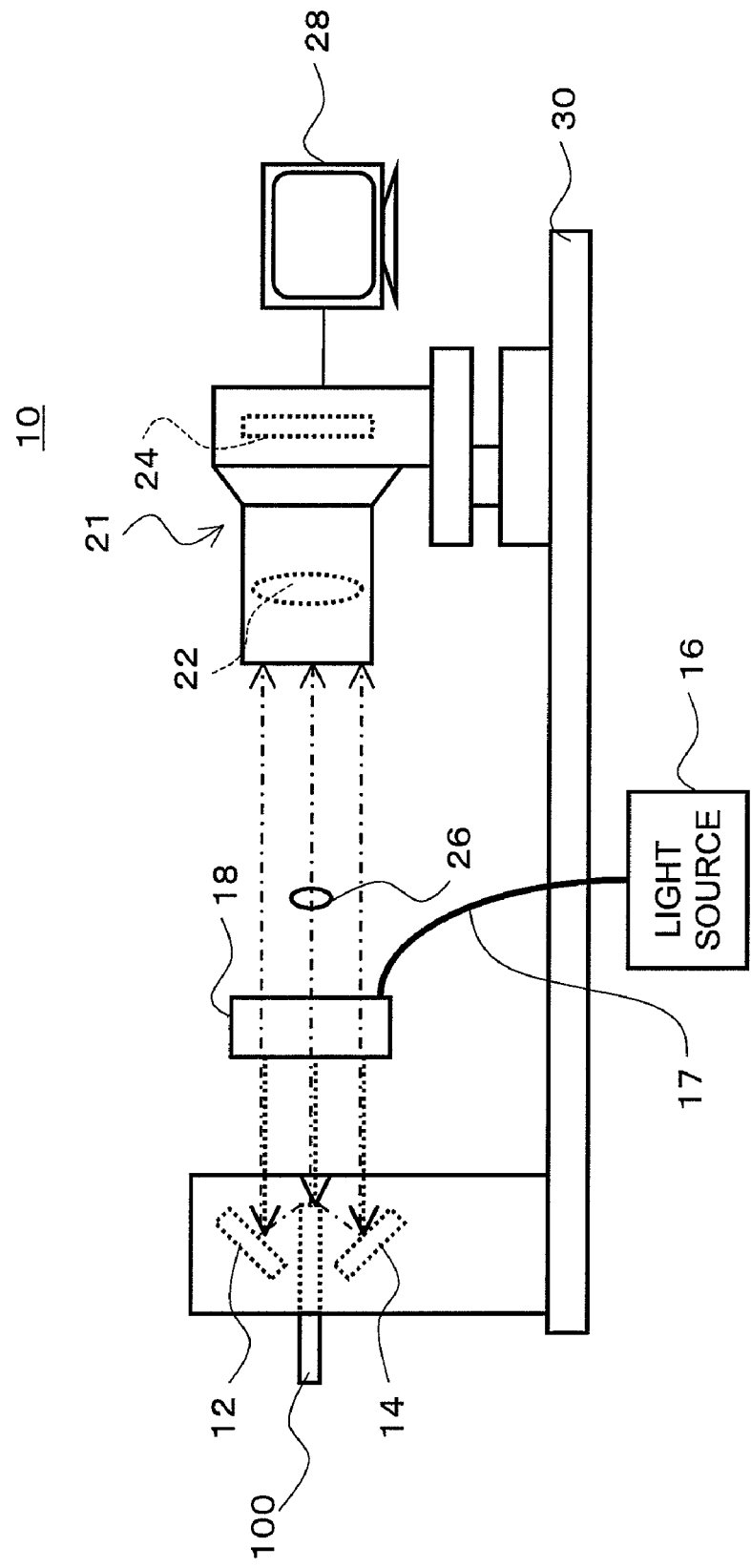
FIG. 1 A view showing the configuration of a semiconductor wafer inspection apparatus according to an embodiment of the present invention.

10 semiconductor wafer inspection apparatus
12, 14 mirror 12a, 14a reflection surface
16 light source
17 optical fiber
17a illuminating surface
18 illumination light guide lamp part
19 half mirror
20 cylindrical planoconvex lens
21 camera
22 camera lens
24 imaging surface
26 correction lens
28 monitor
30 guide rail
32, 34 support parts
36, 37 shafts
40, 41, 42, 43 leg parts
100 semiconductor wafer
101 outer circumference edge part
101a outer circumference end face
101b first outer circumference bevel surface
101c second outer circumference bevel surface
102a first main surface
102b second main surface

DESCRIPTION OF EMBODIMENTS

Below, embodiments of the present invention will be explained using the drawings.

FIG. 1 is a view showing the configuration of the semiconductor wafer inspection apparatus used as the surface inspection apparatus according to an embodiment of the present invention. The semiconductor wafer inspection apparatus 10 shown in FIG. 1 captures an image of an outer circumference edge part of a plate-shaped member constituted by a semiconductor wafer 100 and inspects the damage, projections, and other conditions at the outer circumference edge part. Further, in this semiconductor wafer inspection apparatus 10, the semiconductor wafer 100 is supported in a rotatable manner by a rotational mechanism (not shown) set on a guide rail 30. A camera 21 is provided movably on the guide rail so as to face the outer circumference edge part of the semiconductor wafer 100. A light source 16 (for example, metal halide light source) and an illumination light guide lamp part 18 are connected by a plurality of optical fibers 17 (constitution of illumination unit). Light emitted from the light source 16 passes through the plurality of optical fibers 17 and reaches the illumination light guide lamp part 18. The illumination light guide lamp part 18 is set so that light transmitted over the plurality of optical fibers 17 is projected onto the outer circumference edge part of the semiconductor wafer 100. As explained later, to enable a plurality of surfaces of the outer circumference edge part of the semiconductor wafer 100 facing different directions to be caught by a single camera 21, a mirror 12 (first optical member) and a mirror 14 (second optical member) are provided near the outer circumference edge part of the semiconductor wafer 100 and a correction lens 26 (third optical member) is provided between the semiconductor wafer 100 and camera 21. The camera 21 has a camera lens 22 and imaging surface 24. Note that, this semiconductor wafer inspection apparatus 10 has a monitor 28 for displaying an image obtained by the camera 21.

Figure 2A:
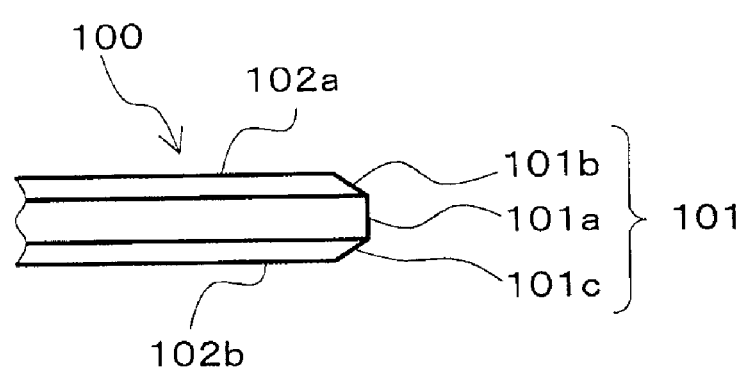
FIG. 2A A partial side view showing the structure of an outer circumference edge part of a semiconductor wafer to be inspected.
Figure 2B:
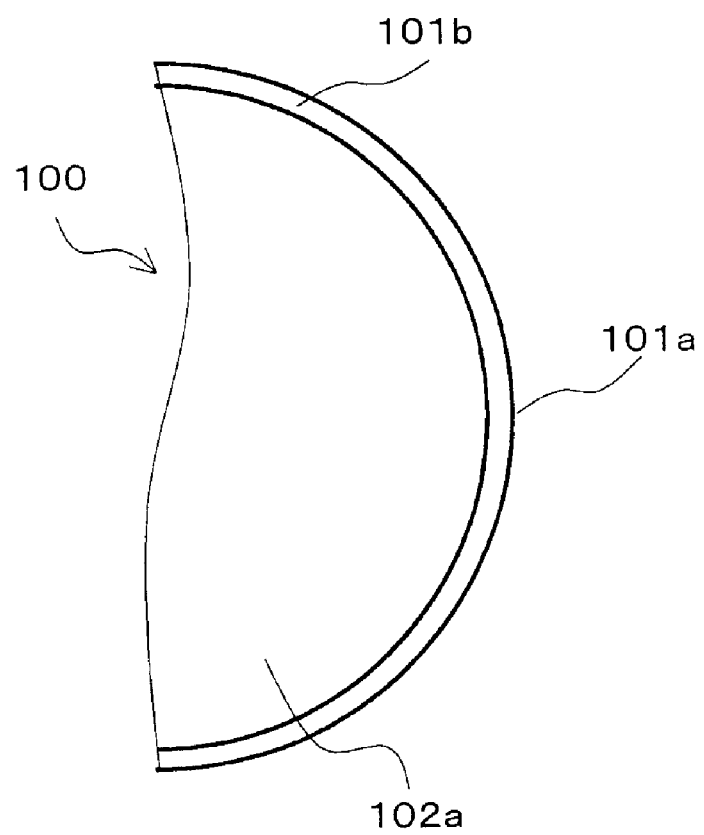
FIG. 2B A partial plan view showing a first main surface (front surface) of a semiconductor wafer to be inspected.

FIG. 2A is a side view showing the structure of the outer circumference edge part of the semiconductor wafer 100 to be inspected, while FIG. 2B is a partial plan view showing a first main surface (front surface) of the semiconductor wafer 100. The semiconductor wafer 100 shown in FIG. 2A and FIG. 2B is chamfered at the outer circumference edge part 101 to prevent damage. Specifically, the outer circumference edge part 101 is comprised of the outer circumference end face 101a vertical to the first main surface 102a and second main surface 102b, the first outer circumference bevel surface 101b slanted at the outer edge of the first main surface 102a, and the second outer circumference bevel surface 101c slanted at the outer edge of the second main surface 102b.

Figure 3:
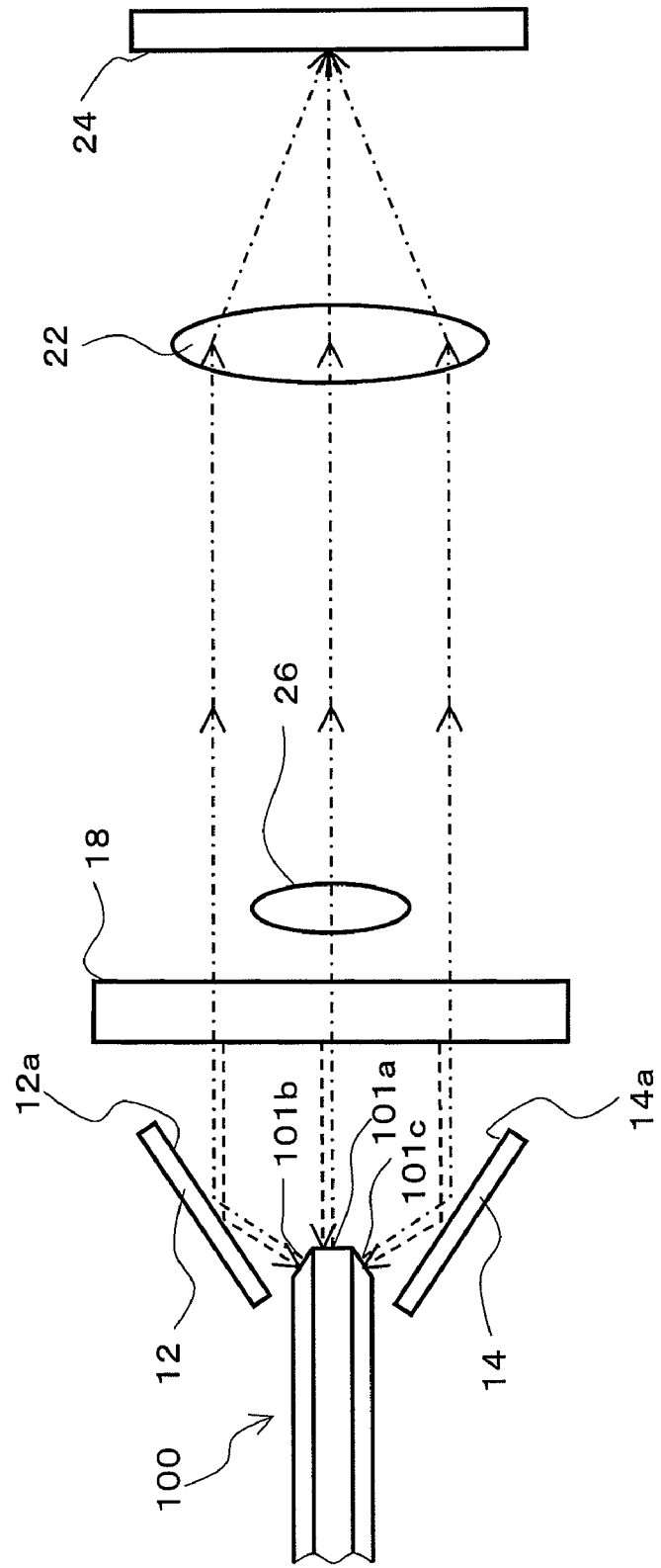
FIG. 3 A view of the arrangement of parts of an optical system in a semiconductor wafer inspection apparatus as seen from the side.
Figure 4:
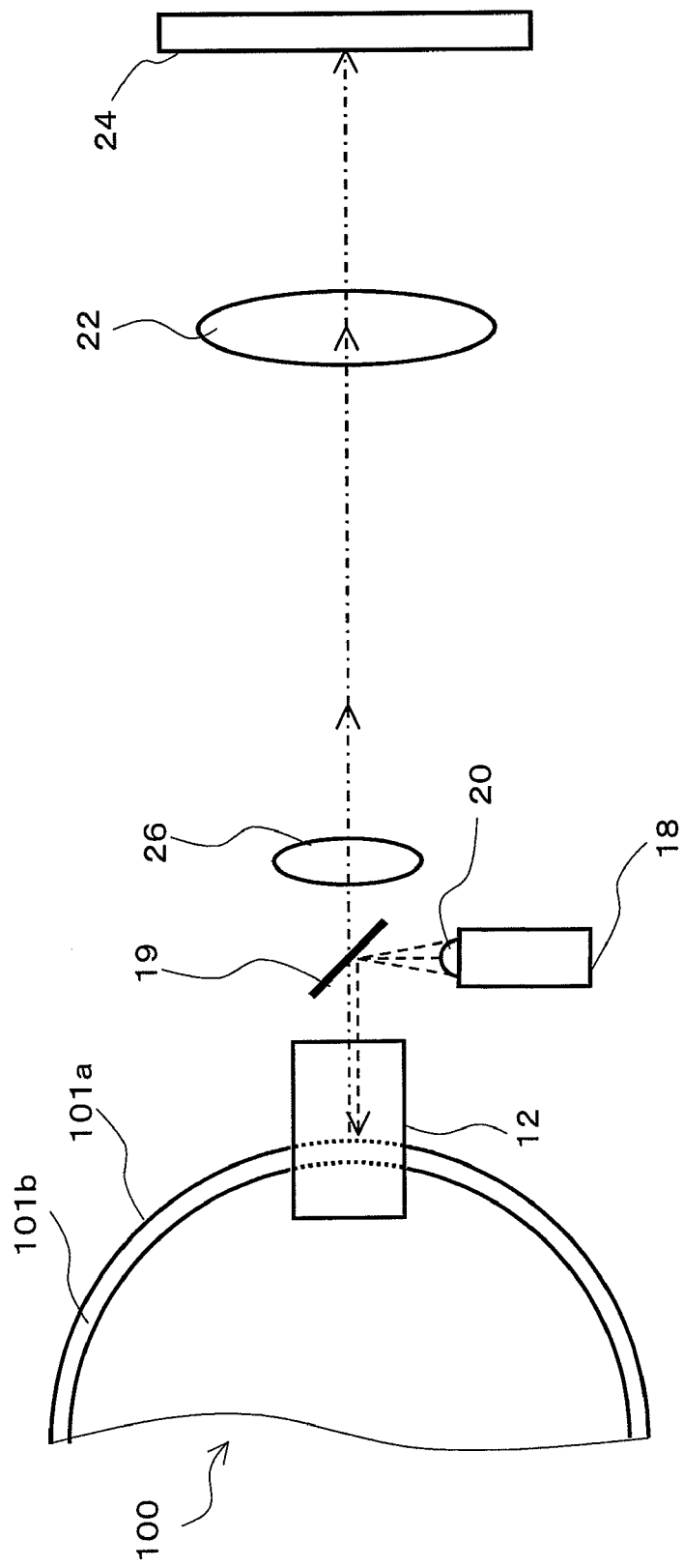
FIG. 4 A view of the arrangement of parts of an optical system in a semiconductor wafer inspection apparatus as seen from above FIG. 5 A view showing the change in lightness of the image formed at the imaging surface in the case where an illumination light guide lamp part irradiates light of a constant illuminance distribution.

FIG. 3 and FIG. 4 show the arrangement of the parts of the optical system in the semiconductor wafer inspection apparatus 10, where FIG. 3 is a view of that arrangement seen from the side and FIG. 4 is a view of that arrangement seen from above. As shown in FIG. 3 and FIG. 4, the camera lens 22 of the camera 21 is arranged facing the outer circumference end face 101a of the outer circumference edge part 101 of the semiconductor wafer 100. The imaging surface 24 of the camera 21 is arranged at the opposite side of the camera lens 22 from the outer circumference end face 101a of the outer circumference edge part 101 of the semiconductor wafer 100.

The mirror 12 is arranged above the first outer circumference bevel surface 101b of the semiconductor wafer 100 so that its reflection surface 12a is slanted toward the camera lens 22 side. On the other hand, the mirror 14 is arranged below the second outer circumference bevel surface 101c of the semiconductor wafer 100 so that its reflection surface 14a is slanted toward the camera lens 22 side. These mirrors 12 and 14 can be adjusted in slant angles by a later explained adjustment mechanism.

The illumination light guide lamp part 18 irradiates light received from the light source 16 through the plurality of optical fibers 17 from illuminating surfaces constituted by the front ends of the plurality of optical fibers 17. This irradiated light travels in parallel to the line connecting the camera lens 22 and the outer circumference end face 101a of the semiconductor wafer 100 (optical axis of camera lens 22) and reaches the outer circumference edge part 101 of the semiconductor wafer 100 by so-called "coaxial irradiation". Specifically, the half mirror 19 is arranged with a slant angle of 45 degrees with respect to the optical axis of the camera lens 22, while the illumination light guide lamp part 18 is arranged so that the illuminating surfaces of the front ends of the plurality of optical fibers 17 face the half mirror 19 and the irradiating direction of the light becomes a direction perpendicular to the optical axis of the camera lens 22 (see FIG. 4). In front of the illuminating surfaces of the illumination light guide lamp part 18, the cylindrical planoconvex lens 20 is arranged so that the illuminating surface side is flat. The light irradiated from the illuminating surfaces of the front ends of the plurality of optical fibers 17 is irradiated via the cylindrical planoconvex lens 20 to the half mirror 19. At this time, the light is focused by the cylindrical planoconvex lens 20 on the reflection surface of the half mirror 19. Further, the light reflected by the half mirror 19 is projected onto the outer circumference end face 101a of the semiconductor wafer 100 and is projected via the reflection surface 12a of the mirror 12 and the reflection surface 14b of the mirror 14 on the first outer circumference bevel surface 101b and the second outer circumference bevel surface 101c of the semiconductor wafer 100. Note that, the positional relationship between the light source 16 and the camera 21 can be set so that the light from the illuminating surfaces of the optical fibers 17 strikes the outer circumference end face 101a of the semiconductor wafer 100 by an angle with respect to the optical axis of the camera lens 22. In this case, the positional relationship between the light source 16 (the illuminating surfaces 17a of the optical fibers 17) and the camera 21 (lens 22) may be one where the camera 21 (lens 22) is arranged in a direction where the light from the illuminating surfaces proceeds by being reflected forward at the outer circumference end face 101a of the semiconductor wafer 100 (relationship of arrangement in brightness field) or, if in a certain range, may be one where it is arranged in a direction offset from the direction where the light proceeds reflected forward (relationship of arrangement in brightness field).

In the state with light irradiated from the illumination light guide lamp part 18, the image of the first outer circumference bevel surface 101b of the semiconductor wafer 100, as shown by the dot-dash lines of FIG. 3 and FIG. 4, is reflected by the reflection surface 12a of the mirror 12 and guided to the top part of the camera lens 22 constituting the first peripheral part. Similarly, the image of the second outer circumference bevel surface 101c of the semiconductor wafer 100, as shown by the dot-dish lines of FIG. 3 and FIG. 4, is reflected at the reflection surface 14a of the mirror 14 and guided to the bottom part of the camera lens 22 constituting the second peripheral part.

Further, in the state with light irradiated from the illumination light guide lamp part 18, the image of the outer circumference end face 101a of the semiconductor wafer 100, as shown by the dot-dash lines of FIG. 3 and FIG. 4, is guided to the correction lens 26. The correction lens 26 is arranged between the camera lens 22 and the outer circumference end face 101a of the semiconductor wafer 100. The image of the outer circumference end face 101a of the semiconductor wafer 100 guided to the correction lens 26 is guided to the center part of the camera lens 22. Due to the correction lens 26, the length of the light path from the outer circumference end face 101a of the semiconductor wafer 100 to the camera lens 22, the length of the light path from the first outer circumference bevel surface 101b of the semiconductor wafer 100 through the reflection surface 12a of the mirror 12 to the camera lens 22, and the length of the light path from the second outer circumference bevel surface 101c of the semiconductor wafer 100 through the reflection surface 14a of the mirror 14 to the camera lens 22 can be made to match.

The image of the outer circumference end face 101a of the semiconductor wafer 100, the image of the first outer circumference bevel surface 101b, and the image of the second outer circumference bevel surface 101c which images are guided to the camera lens 22 are further guided to the imaging surface 24. By having the imaging surface 24 arranged at the focal position, the image of the outer circumference end face 101a of the semiconductor wafer 100, the image of the first outer circumference bevel surface 101b, and the image of the second outer circumference bevel surface 101c are formed at that imaging surface 24. The camera 21 outputs image information corresponding to the images formed on the imaging surface 24 to the monitor 28 whereupon the monitor 28 displays images corresponding to the input image information.

Figure 5:
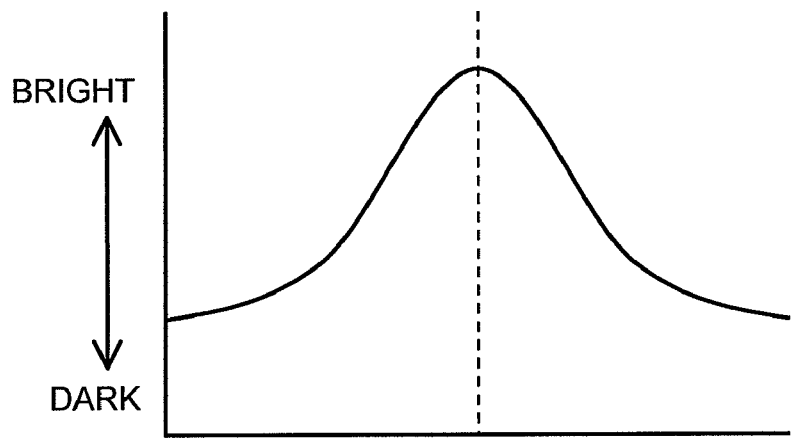

Next, details of the illumination light guide lamp part 18 will be explained. FIG. 5 is a view showing changes in lightness of an image formed on the imaging surface 24 in the case where the illumination light guide lamp part 18 irradiates light of a constant illuminance distribution. As shown in FIG. 5, the image formed on the imaging surface 24 has the characteristic, due to the aberration between the center part and peripheral parts of the camera lens 22, of the image formed through the center part of the camera lens 22 being higher in lightness and the images formed through the peripheral parts of the camera lens 22 (top and bottom) being lower in lightness.

Figure 6:
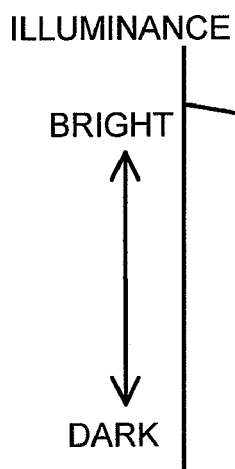
FIG. 6 A view showing the illuminance distribution of light irradiated by the illumination light guide lamp part.

The illumination light guide lamp part 18, in view of this characteristic of the camera lens 22, irradiates light of an illuminance distribution having a relationship reverse to the relationship of lightness of the image formed on the imaging surface 24 in the case of the illumination light guide lamp part 18 irradiating light of a constant illuminance distribution. FIG. 6 is a view showing the illuminance distribution of light irradiated by the illumination light guide lamp part 18. As shown in FIG. 6, the illumination light guide lamp part 18 irradiates light so that the illuminance of light irradiated by the illuminating surfaces arranged at the center part among the plurality of illuminating surfaces of the front ends of the plurality of optical fibers 17 arranged, in other words, the light projected onto the outer circumference end face 101a of the semiconductor wafer 100, becomes smaller than the illuminance of the light irradiated from the illuminating surfaces arranged at the end parts, in other words, the light projected via the reflection surface 12a of the mirror 12 and the reflection surface 14b of the mirror 14 onto the first outer circumference bevel surface 101b and second outer circumference bevel surface 101c of the semiconductor wafer 100.

Figure 7A:
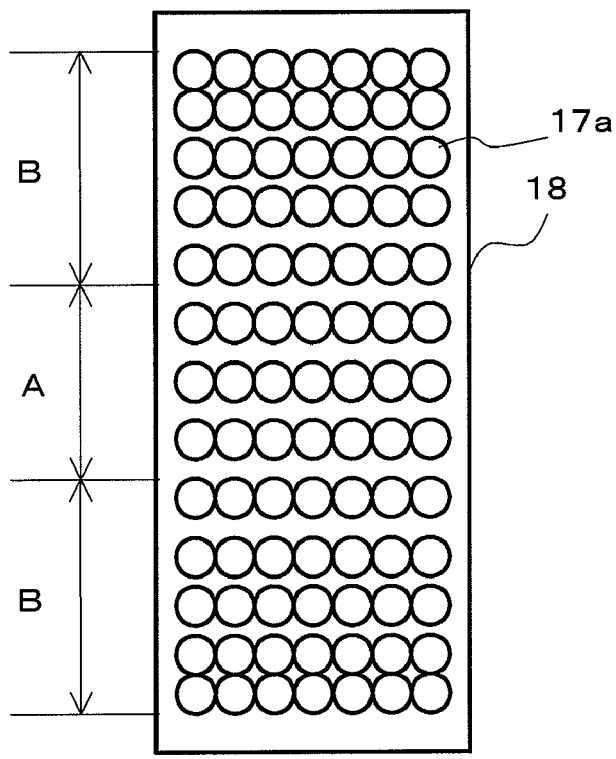
FIG. 7A A view showing a first example of the arrangement of a plurality of illuminating surfaces at the illumination light guide lamp part.
Figure 7B:
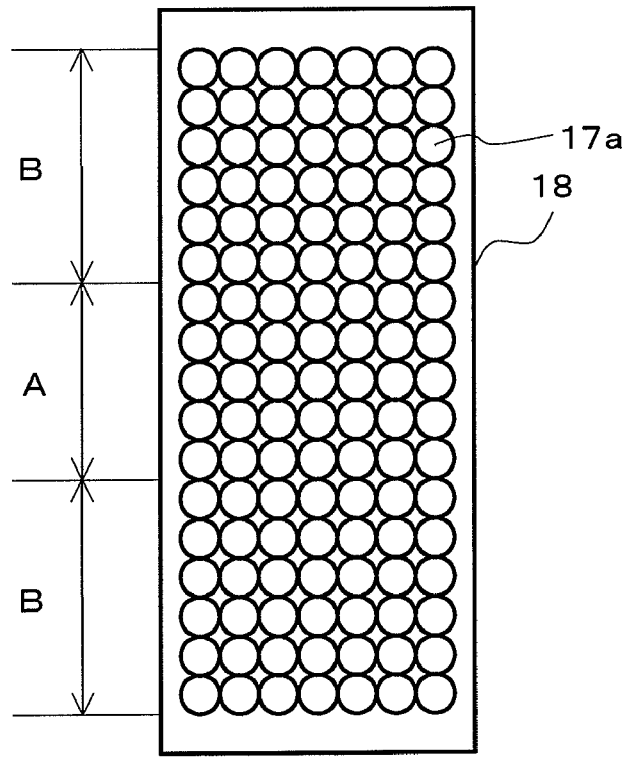
FIG. 7B A view showing a second example of the arrangement of a plurality of illuminating surfaces at the illumination light guide lamp part.

FIG. 7A is a view showing a first example of arrangement of a plurality of illuminating surfaces of front ends of the plurality of optical fibers 17 in the illumination light guide lamp part 18, while FIG. 7B is a view showing a second example of arrangement of a plurality of illuminating surfaces of front ends of the plurality of optical fibers 17 in the illumination light guide lamp part 18. In FIG. 7A and FIG. 7B, the illuminating surfaces 17a in the range A project light onto the outer circumference end face 101a of the semiconductor wafer 100, while the illuminating surfaces 17a in the range B project light via the reflection surface 12a of the mirror 12 and the reflection surface 14b of the mirror 14 onto the first outer circumference bevel surface 101b and second outer circumference bevel surface 101c of the semiconductor wafer 100.

In the example shown in FIG. 7A, the illuminating surfaces 17a of both the range A and range B are arranged at equal intervals. In this case, by minimizing the illuminance of the light irradiated by the illuminating surfaces 17a arranged at the center part, gradually increasing the illuminance of light irradiated by the illuminating surfaces 17a the more toward the end parts, and maximizing the illuminance of the light irradiated by the illuminating surfaces 17a arranged at the end parts, it is possible to realize the illuminance distribution shown in FIG. 6. On the other hand, in the example shown in FIG. 7B, the illuminating surfaces 17a are wide in placement pitch and small in placement density at the center part. The placement pitch becomes narrower and the placement density higher the more toward the end parts. In this case, it is possible to make the illuminance of light irradiated from all illuminating surfaces 17a identical and realize the illuminance distribution shown in FIG. 6.

Note that, the illuminance distribution of the light irradiated by the illumination light guide lamp part 18 does not necessarily have to be the reverse relationship to the lightness of the images formed at the imaging surface 24 as shown in FIG. 6 and may also be close to a reverse relationship.

Figure 8A:
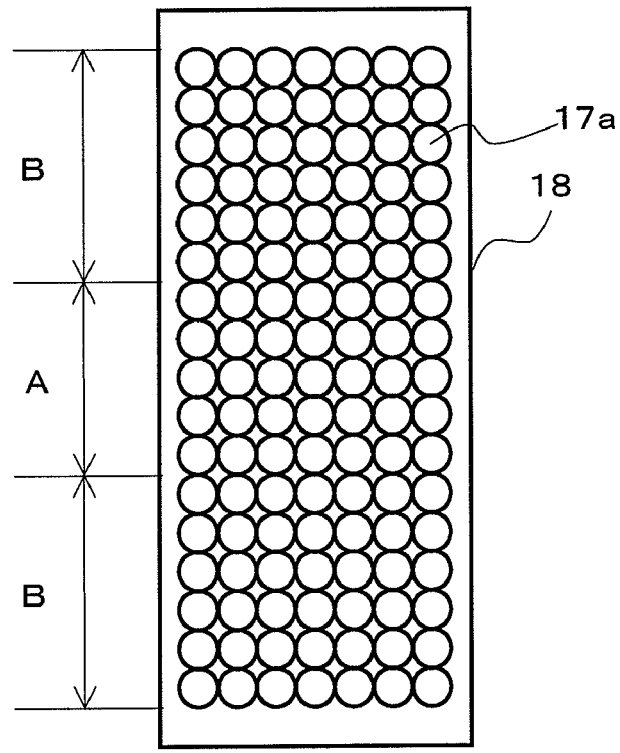
FIG. 8A A view showing a third example of the arrangement of a plurality of illuminating surfaces at the illumination light guide lamp part.
Figure 8B:
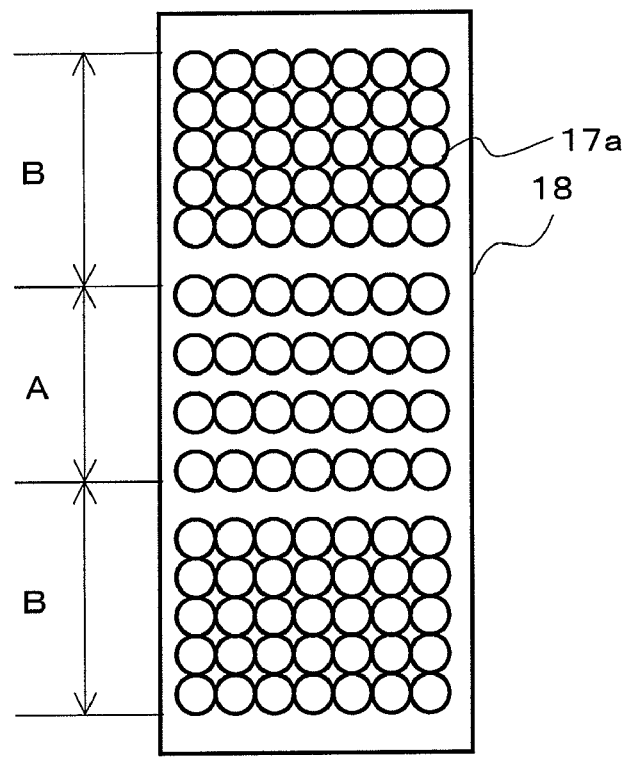
FIG. 8B A view showing a fourth example of the arrangement of a plurality of illuminating surfaces at the illumination light guide lamp part.

FIG. 8A is a view showing a third example of arrangement of a plurality of illuminating surfaces of front ends of the plurality of optical fibers 17 in the illumination light guide lamp part 18, while FIG. 8B is a view showing a fourth example of arrangement of a plurality of illuminating surfaces of front ends of the plurality of optical fibers 17 in the illumination light guide lamp part 18. In the same way as the case shown in FIG. 7A and FIG. 7B, in FIG. 8A and FIG. 8B, the illuminating surfaces 17a in the range A project light at the outer circumference end face 101a of the semiconductor wafer 100, while the illuminating surfaces 17a in the range B project light through the reflection surface 12a of the mirror 12 and the reflection surface 14b of the mirror 14 to the first outer circumference bevel surface 101b and second outer circumference bevel surface 101c of the semiconductor wafer 100.

In the example shown in FIG. 8A, the placement pitch of the illuminating surfaces 17a is made a two-stage one. The placement pitch is broad and the placement density small in the range A, while the placement pitch is narrow and the density large in the range B. In this case, it is possible to make the illuminance of light irradiated from all illuminating surfaces 17a identical and realize a change in illuminance close to FIG. 6. On the other hand, in the example shown in FIG. 8B, the illuminating surfaces 17a of both of the range A and range B are arranged at equal pitches. In this case, by making the illuminance of the light irradiated from the illuminating surfaces 17a of the range A smaller than the illuminance of the light irradiated from the illuminating surfaces 17a of the range B, it is possible to realize a change of illuminance close to FIG. 6.

As shown in FIG. 7A, arranging the plurality of illuminating surfaces 17a at equal pitches, minimizing the illuminance of the light irradiated from the illuminating surfaces 17a arranged at the center part, and gradually increasing the illuminance of the light irradiated from the illuminating surfaces 17a toward the end parts so as to maximum the illuminance of the light irradiated from the illuminating surfaces 17a arranged at the end parts or, as shown in FIG. 8B, arranging the plurality of illuminating surfaces 17a at equal pitches and making the illuminance of the light irradiated by the illuminating surfaces 17a of the range A smaller than the illuminance of the light irradiated by the illuminating surfaces 17a of the range B, for example, as shown below, can be realized by suitably rearranging the optical fibers 17.

Figure 9:
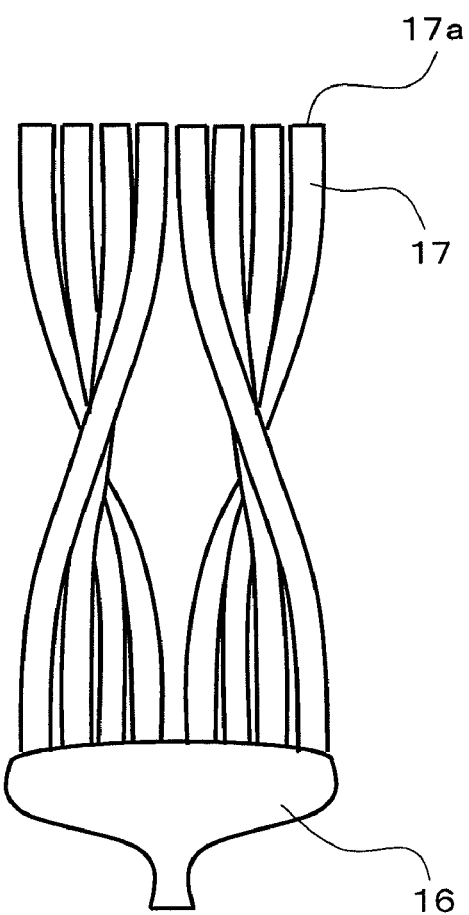
FIG. 9 A view showing an example of the arrangement of optical fibers.

FIG. 9 is a view showing an example of rearrangement of the optical fibers 17. In FIG. 9, the plurality of optical fibers 17 are rearranged so that the closer they are connected to the center part of the light source 16, the more to the end parts the positions of arrangement of the illuminating surfaces 17a of the optical fibers 17 at the illumination light guide lamp part 18. By rearranging them in this way, when the light source 16 has the characteristic of the illuminance of light irradiated from the center part being large and the illuminance of light irradiated from the end parts being small, in the illumination light guide lamp part 18, light of a small illuminance will be irradiated from the illuminating surfaces 17a arranged at the center part, while light of a large illuminance will be irradiated from the illuminating surfaces 17a arranged at the end parts.

Figure 10:
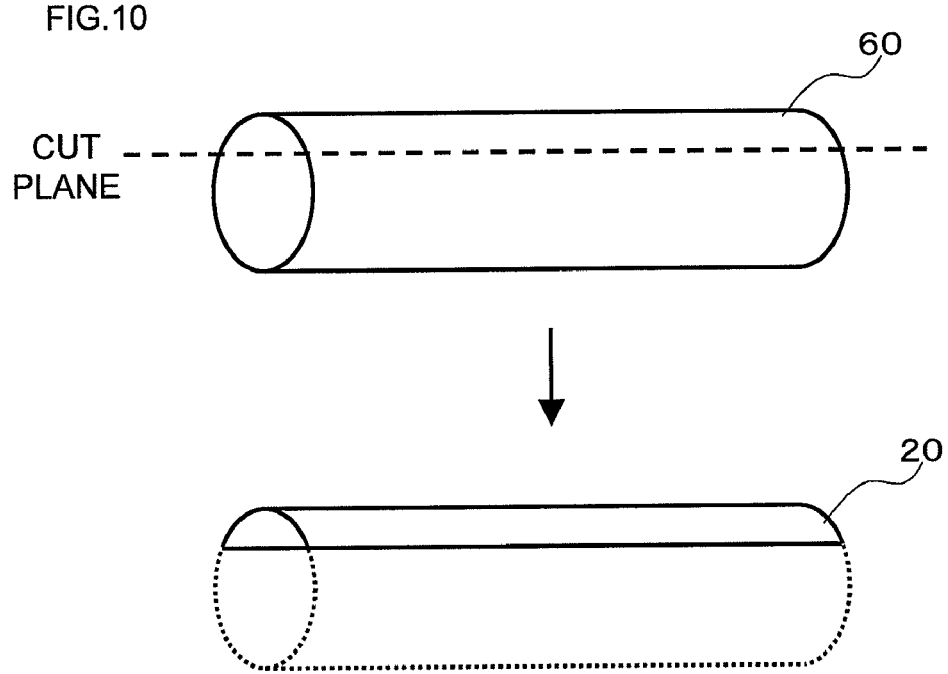
FIG. 10 A view showing a process of production of a cylindrical planoconvex lens.

Further, in front of the illuminating surfaces 17a at the illumination light guide lamp part 18, the cylindrical planoconvex lens 20 is arranged (see FIG. 4). FIG. 10 is a view showing the process of production of a cylindrical planoconvex lens. As shown in FIG. 10, the cylindrical planoconvex lens 20 is formed by cutting a glass, plastic, or other transparent member cylinder 60 straight along the direction of extension (direction perpendicular to circular shape first main surface and second main surface).

Figure 11A:
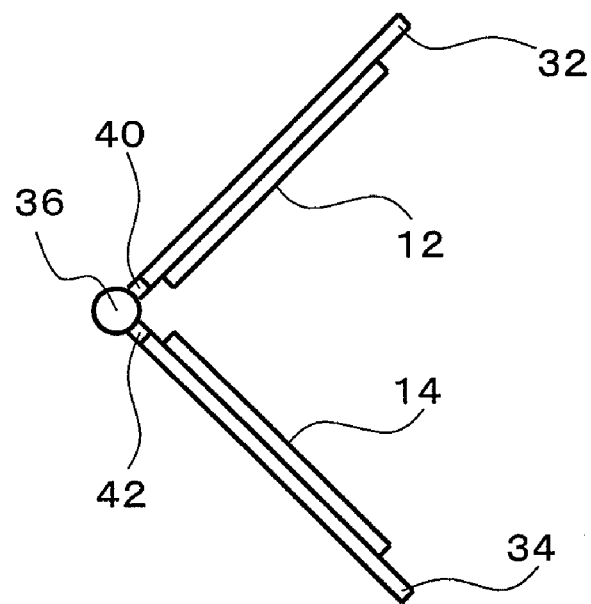
FIG. 11A A side view showing an example of a mechanism for adjustment of a slant angle of a mirror.
Figure 11B:
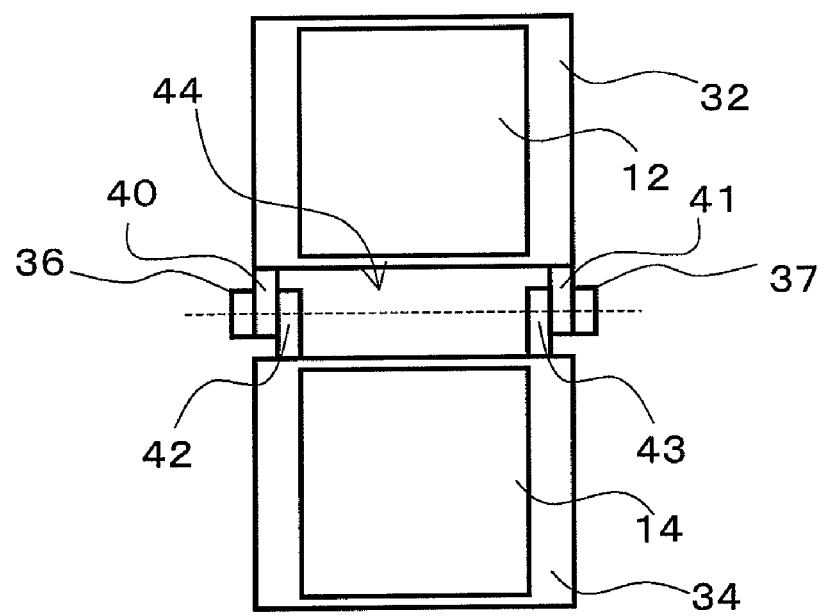
FIG. 11B A front view showing an example of a mechanism for adjustment of a slant angle of a mirror.

FIG. 11A is a side view showing an example of a mechanism for adjustment of the slant angles of the mirrors 12 and 14, while FIG. 11B is a front view showing an example of a mechanism for adjustment of the slant angles of the mirrors 12 and 14. As shown in FIG. 11A and FIG. 11B, this adjustment mechanism is comprised of support parts 32 and 34, shafts 36, 37, and leg parts 40, 41, 42, and 43.

The support part 32 has the mirror 12 attached to it and supports that mirror 12. Further, the support parts 32 is provided with a leg part 40 at one end of its bottom part and is provided with a leg part 41 at the other end. The leg part 40 is attached to be able to rotate about a shaft 36, while the leg part 41 is attached to be able to rotate about a shaft 37. On the other hand, the support part 34 has the mirror 14 attached to it and supports that mirror 14. Further, the support parts 34 is provided with a leg part 42 at one end of its top part and is provided with a leg part 43 at the other end. The leg part 42 is attached to be able to rotate about the shaft 36, while the leg part 43 is attached to be able to rotate about the shaft 37.

By such a structure, the mirrors 12 and 14 can be freely adjusted in slant angles about the shafts 36 and 37. By adjusting the slant angles of the mirrors 12 and 14, it is possible to guide the images of the first outer circumference bevel surface 101b and second outer circumference bevel surface 101c of the semiconductor wafer 100 to the camera lens 22. Further, a gap 44 is formed between the bottom part of the support part 32 and the top part of the support part 34. By arranging the end part of the semiconductor wafer 100 in this gap 44, the image of the first outer circumference bevel surface 101b of the semiconductor wafer 100 can be reliably guided to the mirror 12 and the image of the second outer circumference bevel surface 101c can be reliably guided to the mirror 14.

In this way, the semiconductor wafer inspection apparatus 10 of the present embodiment has the characteristic that, when the illumination light guide lamp part 18 irradiates light of a constant illuminance distribution, the image of the outer circumference end face 101a of the semiconductor wafer 100 formed on the imaging surface 24 via the center part of the camera lens 22 is high in lightness, while the images of the first outer circumference bevel surface 101b of the semiconductor wafer 100 and the second outer circumference bevel surface 101c formed on the imaging surface 24 via the peripheral parts are low in lightness. In view of this, the illumination light guide lamp part 18 illuminates the outer circumference end face 101a, first outer circumference bevel surface 101b, and second outer circumference bevel surface 101c so that compared with the outer circumference end face 101a of the semiconductor wafer 100, the first outer circumference bevel surface 101b and the second outer circumference bevel surface 101c become brighter.

Figure 12A:
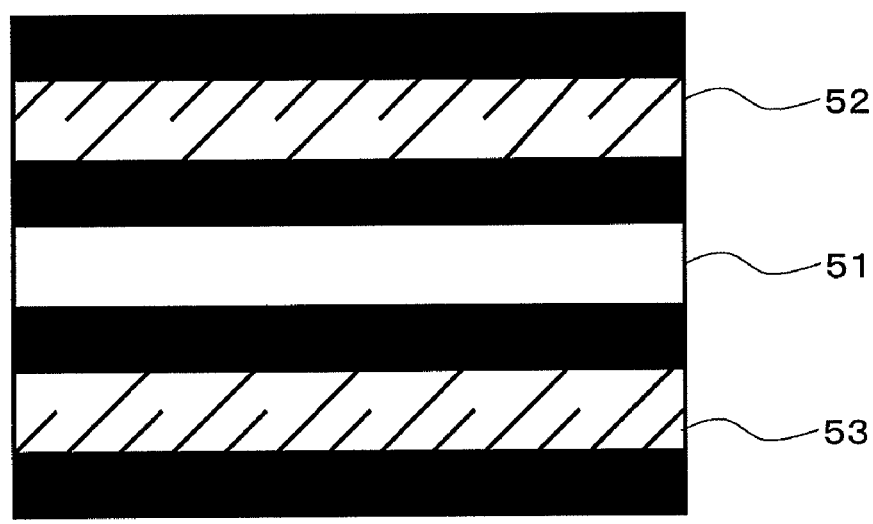
FIG. 12A A view showing images of an outer circumference end face, first outer circumference bevel surface, and second outer circumference bevel surface in a conventional semiconductor wafer inspection apparatus.
Figure 12B:
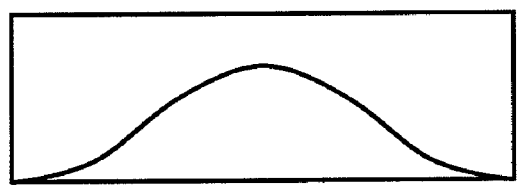
FIG. 12B A view showing an illuminance characteristic of an illumination light guide lamp part.
Figure 12C:
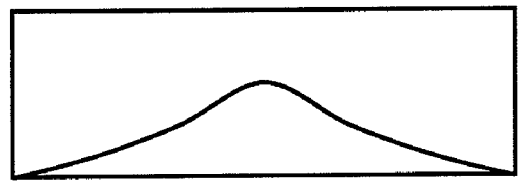
FIG. 12C A view showing a lightness characteristic of an image formed through a camera lens.
Figure 12D:
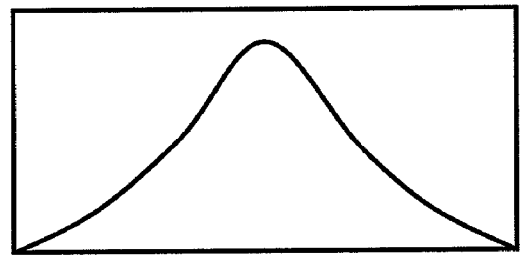
FIG. 12D A view showing a lightness characteristic of an image.

FIG. 12A is a view showing the images of the outer circumference end face, first outer circumference bevel surface, and second outer circumference bevel surface in a conventional semiconductor wafer inspection apparatus, FIG. 12B is a view showing the illuminance characteristic of an illumination unit, FIG. 12C is a view showing the lightness characteristic of an image formed via a camera lens, and FIG. 12D is a view showing the lightness characteristic of an image. In the past, as shown in FIG. 12B, the illuminance of an illumination unit was high at the center part and became lower the more toward the end parts and, as shown in FIG. 12C, the lightness of the image via the center part of the camera lens was high and the lightness of the image via the peripheral parts became lower the more toward those parts. Due to the superposition of the illuminance characteristic of such an illumination unit and the lightness characteristic of the image formed via the camera lens, as shown in FIG. 12A, the image 51 of the outer circumference end face 101a of the semiconductor wafer 100 becomes high in lightness, the image 52 of the first outer circumference bevel surface 101b of the semiconductor wafer 100 and the image 53 of the second outer circumference bevel surface 101c become lower in lightness and along with this, as shown in FIG. 12D, the lightness of the image also becomes high at the center part and becomes lower the more toward the end parts.

Figure 13A:
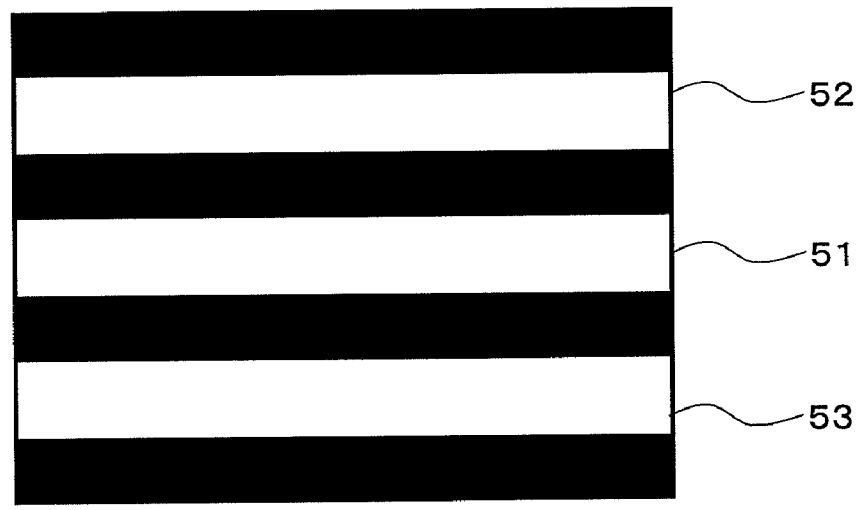
FIG. 13A A view showing images of an outer circumference end face, first outer circumference bevel surface, and second outer circumference bevel surface in the semiconductor wafer inspection apparatus of the present embodiment.
Figure 13B:
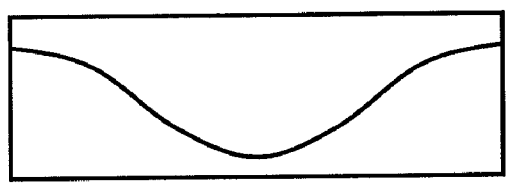
FIG. 13B A view showing an illuminance characteristic of an illumination light guide lamp part.
Figure 13C:
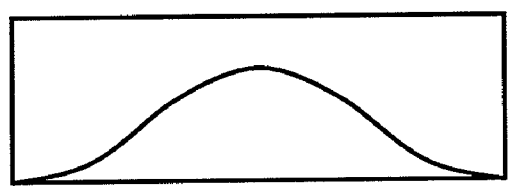
FIG. 13C A view showing a lightness characteristic of an image formed through a camera lens.
Figure 13D:
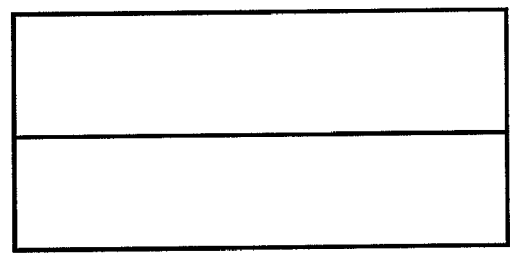
FIG. 13D A view showing a lightness characteristic of an image.

On the other hand, FIG. 13A is a view showing the images of the outer circumference end face 101a, first outer circumference bevel surface 101b, and second outer circumference bevel surface 101c in the semiconductor wafer inspection apparatus of the present embodiment 10, FIG. 13B is a view showing the illuminance characteristic of the illumination light guide lamp part 18, FIG. 13C is a view showing the lightness characteristic of the image formed through the camera lens 22, and FIG. 13D is a view showing the lightness characteristic of the image. In the same way as in the past, as shown in FIG. 13C, the image via the center part of the camera lens 22 is high in lightness, while the images via the peripheral parts become lower in lightness the more toward the peripheral parts. However, in the semiconductor wafer inspection apparatus of the present embodiment 10, as shown in FIG. 13B, the illuminance characteristic of the illumination unit 16 is set so as to cancel out the lightness characteristic of the image formed via the camera lens 22, so, as shown in FIG. 13A, the lightness of the image 51 of the outer circumference end face 101a of the semiconductor wafer 100 and the lightnesses of the image 52 of the first outer circumference bevel surface 101b and the image 53 of the second outer circumference bevel surface 101c can be made as uniform as possible, in other words, can be made within a predetermined range, and, along with this, as shown in FIG. 13D, the lightness of the image as a whole can be made within a predetermined range. Therefore, even if making the detection conditions of the lightness simple, no over or under lightness occurs at the images 51 to 53 and the state of the outer circumference edge part 101 of the semiconductor wafer 100 can be suitably inspected based on these images 51 to 53.

Note that, in the above embodiment, the case of inspecting the state of the outer circumference edge part 101 of a semiconductor wafer 100 was explained, but the present invention can be similarly applied to the case of inspecting the outer circumference edge part of another plate-shaped member which, in the same way as a semiconductor wafer 100, has an outer circumference edge part comprised of an outer circumference end face, first outer circumference bevel surface, and second outer circumference bevel surface.

Further, in the above-mentioned embodiment, the illumination light guide lamp part 18 irradiates light of an illuminance distribution having a reverse relationship to the relationship of lightness of the images formed on the imaging surface 24 when irradiating light of a constant illuminance distribution or to make the illuminance of the light projected onto the outer circumference end face 101a smaller than the illuminances of the light projected onto the first outer circumference bevel surface 101b and second outer circumference bevel surface 101c, but if the images of the outer circumference end face 101a, first outer circumference bevel surface 101b, and second outer circumference bevel surface 101c formed on the imaging surface 24 have a lightness in a predetermined range, the illuminance distribution of the illumination light guide lamp part 18 is not limited to these illuminance distributions.

Further, in the above embodiment, the semiconductor wafer inspection apparatus 10 has the correction lens 26, while the illumination light guide lamp part 18 has the cylindrical planoconvex lens 20, but the invention may also be configured to not have one or both of these correction lens 26 and cylindrical planoconvex lens 20. Further, in the above embodiment, the light from the light source 16 is irradiated through the optical fibers 17 and from the front ends of the optical fibers 17, that is, the illuminating surfaces 17a, but instead of these light source 16 and optical fibers 17, it is also possible to arrange a plurality of light emitting diodes at the positions of the illuminating surfaces and irradiate light from these light emitting diodes.

INDUSTRIAL APPLICABILITY

The surface inspection apparatus according to the present invention can suitably inspect the outer circumference edge part of a plate-shaped member and is useful as a surface inspection apparatus.

The invention claimed is:

1. A surface inspection apparatus capturing an image of and inspecting an outer circumference edge part including a first outer circumference bevel surface slanted at an outer edge of a first main surface of a plate-shaped member, a second outer circumference bevel surface slanted at an outer edge of a second main surface of said plate-shaped member, and an outer circumference end face of said plate-shaped member, said surface inspection apparatus having
a camera lens arranged facing said outer circumference edge part of said plate-shaped member,
an imaging surface arranged at an opposite side of said camera lens from said outer circumference edge part of the plate-shaped member,
a first optical member forming an image of said first outer circumference bevel surface of said plate-shaped member on said imaging surface via a first peripheral part of said camera lens,
a second optical member forming an image of said second outer circumference bevel surface of said plate-shaped member on said imaging surface via a second peripheral part of said camera lens,
a third optical member forming an image of said outer circumference end face of said plate-shaped member on said imaging surface via a center part of said camera lens, and
an illumination unit illuminating said outer circumference end face, said first outer circumference bevel surface, and said second outer circumference bevel surface so that compared with said outer circumference end face, said first outer circumference bevel surface and said second outer circumference bevel surface become brighter.

2. A surface inspection apparatus as set forth in claim 1, wherein said illumination unit illuminates said outer circumference end face, said first outer circumference bevel surface, and said second outer circumference bevel surface by an illuminance distribution giving a reverse relationship to the relationship of brightness of the image of said outer circumference end face, the image of said first outer circumference bevel surface, and the image of said second outer circumference bevel surface formed on said imaging surface via said camera lens when irradiating light of a constant illuminance distribution.

3. A surface inspection apparatus as set forth in claim 1, wherein said illumination unit has
a light source and
a plurality of illuminating surfaces arranged facing said outer circumference edge part of said plate-shaped member and irradiating light from said light source, and
the illuminance of light irradiated from the illuminating surfaces arranged at the center part among said plurality of illuminating surfaces is smaller than the illuminances of light irradiated from the illuminating surfaces arranged at the end parts.

4. A surface inspection apparatus as set forth in claim 3, wherein said illumination unit has a cylindrical planoconvex lens arranged in front of said plurality of illuminating surfaces, and said illuminating surface side is flat.

5. A surface inspection apparatus as set forth in claim 1, wherein said illumination unit has
  a light source and
  a plurality of illuminating surfaces arranged facing said outer circumference edge part of said plate-shaped member and irradiating light from said light source, and
  a placement density at the center part of said plurality of illuminating surfaces is smaller than the placement densities at the end parts.

6. A surface inspection apparatus as set forth in claim 5, wherein said illumination unit has a cylindrical planoconvex lens arranged in front of said plurality of illuminating surfaces, and said illuminating surface side becomes flat.

* * * * *